United States Patent [19]
McNeal

[11] Patent Number: 4,716,601
[45] Date of Patent: Jan. 5, 1988

[54] TEAR-OFF LENS SYSTEM AND METHOD FOR GOGGLES

[75] Inventor: Joseph R. McNeal, Hailey, Id.

[73] Assignee: Scott USA Limited Partnership, a Washington Limited partnership, Sun Valley, Id.

[21] Appl. No.: 893,508

[22] Filed: Aug. 5, 1986

[51] Int. Cl.$^4$ ............................................. A61F 9/02
[52] U.S. Cl. ..................................................... 2/434
[58] Field of Search ................... 2/434, 424, 438, 439, 2/440, 441, 443, 447, 452, 429, 426, 436, 174, 209, 243 R; 351/47

[56] References Cited

U.S. PATENT DOCUMENTS

| | | | |
|---|---|---|---|
| 3,699,591 | 10/1972 | Breitkopf | 2/243 R |
| 4,076,373 | 2/1978 | Moretti | 2/434 X |
| 4,308,623 | 1/1982 | Voorhees | 2/174 |
| 4,455,689 | 6/1984 | Boyer | 2/434 |
| 4,563,065 | 1/1986 | Kreissl | 351/47 X |

Primary Examiner—Peter Nerbun
Attorney, Agent, or Firm—Jenner & Block

[57] ABSTRACT

This invention provides a stack of tear-off lenses for rapid and easy mounting over a main goggle lens. The invention overcomes the previously discussed disadvantages of excessive mounting time and effort. A method of manufacturing the stack is also provided. In addition, a goggle incorporating the stack of tear-off lenses, as well as a kit for adapting a goggle for tear-off lenses, including the tear-off lens stack and a retaining post member, are disclosed.

25 Claims, 12 Drawing Figures

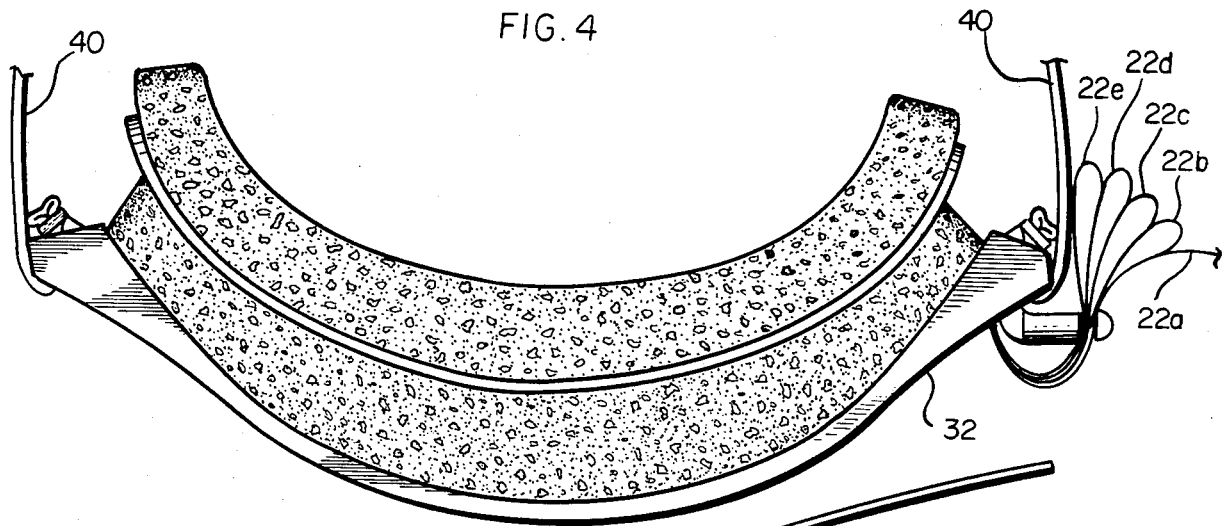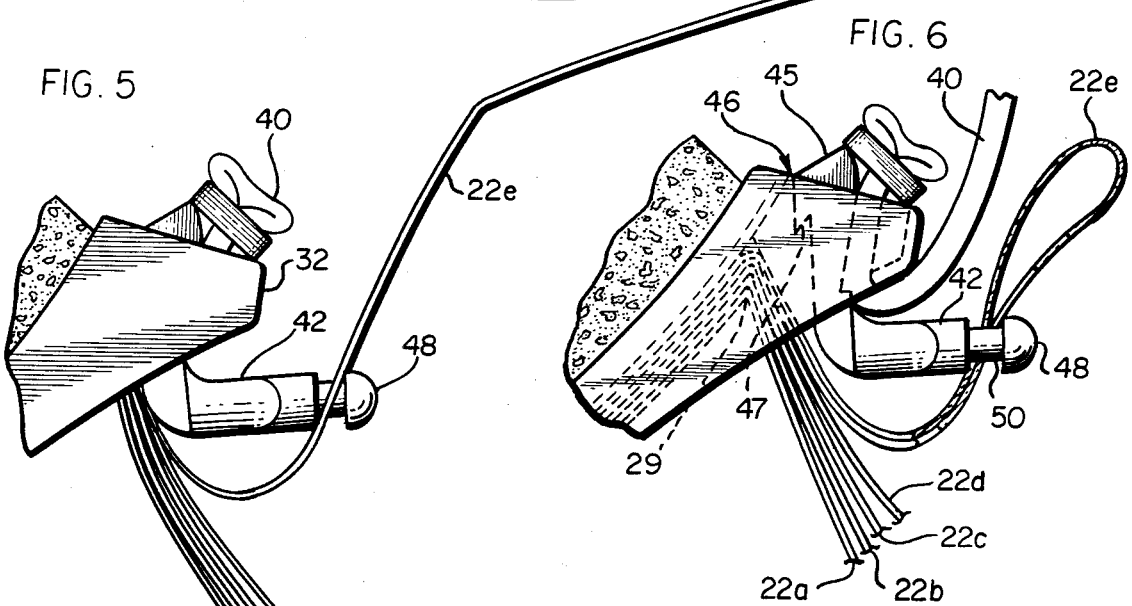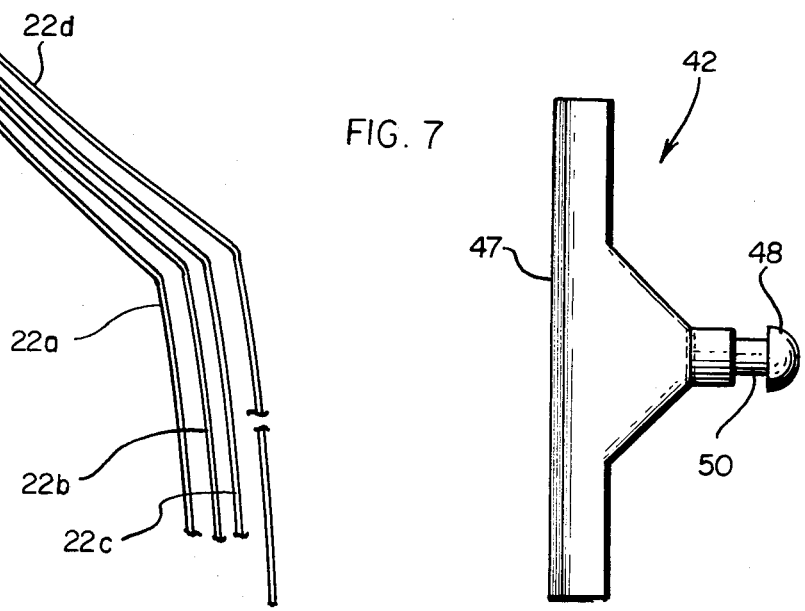

U.S. Patent Jan. 5, 1988 Sheet 3 of 3 4,716,601
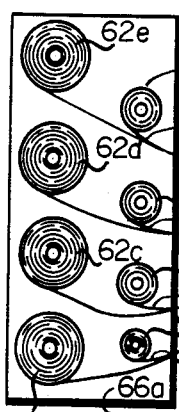
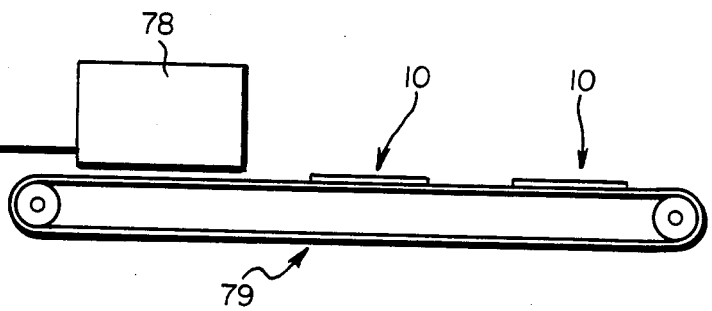
FIG. 8
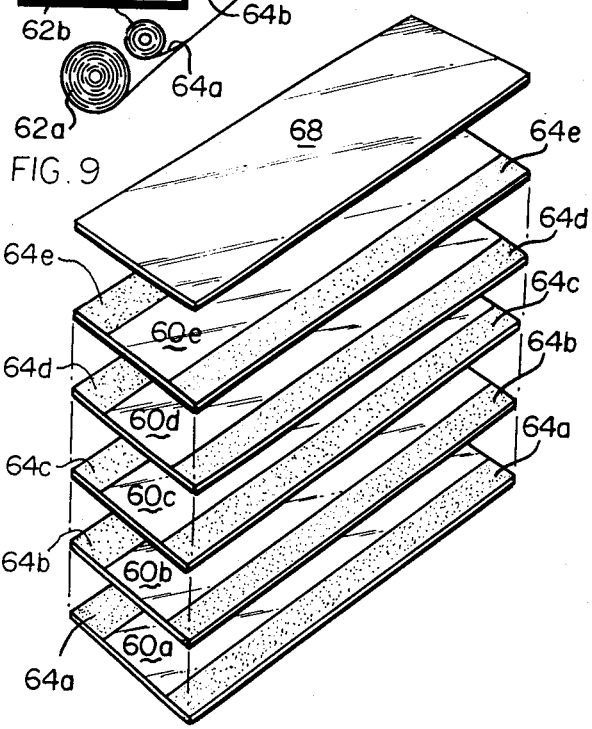
FIG. 9
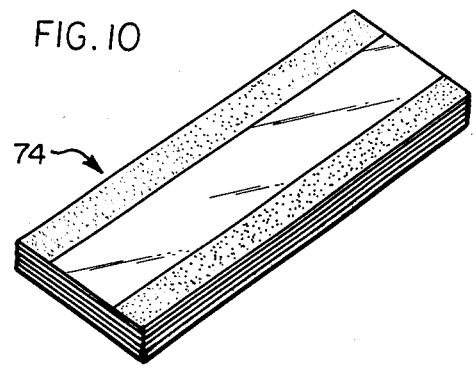
FIG. 10
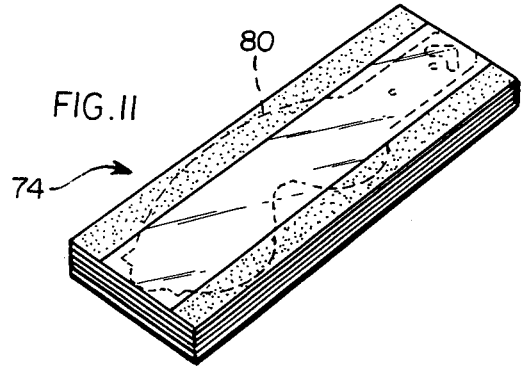
FIG. 11
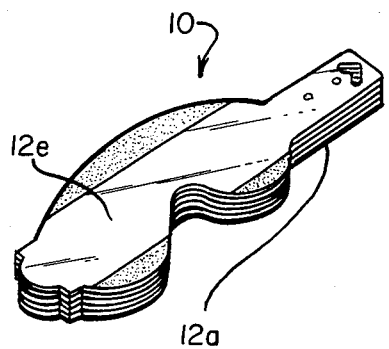
FIG. 12

TEAR-OFF LENS SYSTEM AND METHOD FOR GOGGLES

FIELD OF THE INVENTION

The present invention relates to protective eyewear and, more particularly, to transparencies for goggles which may be readily removed from the lenses thereof.

BACKGROUND OF THE INVENTION

Motorcyclists who use their bikes in off-road activities often find that dirt and debris accumulate on the lens surface of the goggle. This substantially reduces visibility and makes safe operation difficult. Accumulation of debris on the lens surface is a particular problem in activities such as motocrosses and hill climbs. The decreased visibility due to debris, together with the high speed of these events, can produce dangerous operating conditions.

One known solution to this problem, as disclosed in U.S. Pat. No. 4,428,081, is provided by a goggle in which a webbing of transparent material is fed over the goggle lens by means of rollers mounted at the opposite side edges of the goggle frame. When the segment of transparent webbing overlying the lens becomes dirty, the wearer pulls a cord to cause a fresh segment of the transparent webbing to be pulled across the lens. This solution requires an auxiliary mechanical feed mechanism, resulting in additional weight and complexity.

One solution that avoids the need for additional mechanic systems, as disclosed in U.S. Pat. No. 3,945,044, is tear-off transparent lenses. These tear-off lenses comprise individual, thin pieces of transparent plastic material that have the general shape of the goggle lens and which have tabs around their peripheral edges. A plurality of the transparent lenses may be overlaid on the goggle lens by inserting tabs between the lens and the flexible lens frame. When vision is obscured due to accumulation of debris, the wearer can reach up with one hand and tear away the outer tear-off lens. The dirty transparency is discarded and the wearer has a clear view through the lens and remaining unsoiled transparencies.

One principal drawback of the foregoing arrangement is that the transparencies are attached to the lens only by the tabs. In addition, the lenses must be individually mounted.

U.S. Pat. No. 4,455,689 discloses another type of removable transparency. In this patent, a specially configured bracket is inserted through the strap slot on one side of the goggle frame. A plurality of transparencies are then individually installed over the lens. Peripheral tabs on the lens-shaped portion of each transparency are inserted between the lens and the goggle frame. A retaining pin extending from the bracket is forced through a small hole formed in the inner region of an elongated member which extends from one end of the transparency. The elongated member of the transparency is folded back on itself so that the retaining pin extends through a large opening in the outer end of the elongated member. Successive transparencies are similarly mounted. The elongated member of the outermost transparency is not folded but is left free to be grasped with one hand so that the soiled transparency can be torn away from the goggle frame. The elongated member of the outermost transparency that has just been exposed will then automatically extend.

One disadvantage with this type of configuration is that the transparencies must be individually mounted over the lens. The considerable time and effort required to individually position and mount the transparencies can pose a significant drawback if the transparencies have to be mounted just prior to, or during, a race. In addition, individual transparencies are prone to damage due to scratching, for example, and can easily become soiled.

Another type of goggle having a tear off lens, identified as being marketed under the trademark Oakley, is discussed at Column 1, lines 63 et seq. of U.S. Pat. No. 4,455,689. In this goggle, an attachment element with a small round head projects outwardly from the goggle lens adjacent to one side thereof. A plurality of transparencies, each of which has an elongated member which extends beyond the left side edge thereof when viewed from the wearer's perspective, are individually mounted over the lens. The elongated members have a large circular hole adjacent to their outer end and a small hole which tightly fits over the rounded portion of the attachment element. Each of the transparencies has insertion tabs around the peripheral side edges thereof. The transparencies are mounted individually in a manner similar to that described with respect to the goggle disclosed in U.S. Pat. No. 4,455,689, by inserting the tabs between the lens and the lens frame and folding over the elongated portion.

It would therefore be desirable to provide transparencies which can be rapidly mounted on the goggle lens and to minimize the breakage loss associated with individual loose transparencies.

SUMMARY OF THE INVENTION

In accordance with one aspect of the invention, a stack or book of flexible tear-off lenses, adhesively secured together, is provided that can be rapidly and easily mounted over a main goggle lens. The invention overcomes the previously discussed disadvantages of excessive positioning and mounting time. As used herein, "main goggle lens" means the lens of a goggle that is mounted in the goggle, either removably or permanently, and is intended for continued use, alone or in conjunction with disposable tear-off lenses. Since the main lens can become scratched or otherwise damaged after long periods of use, or to change the lens color, these lenses can be removed from the goggle frame and replaced.

In accordance with the invention, the stack of tear-off lenses includes a plurality of flexible transparent lenses that are adhesively bonded together in registry with each other, each having adhesive along upper and lower peripheral portions of each of the lenses. Each of the lenses is manually, serially removable from the lens stack.

Each of the lenses in the stack has a central lens portion, which usually corresponds to the general shape of the main goggle lens, and a securing tab at one end of the tear-off lenses. The securing tabs of the stack are insertable into an opening or slot located in the goggle to facilitate attaching the stack to the frame.

The tear-off lenses each further include an elongated removal tab, usually located at the end opposite the end having the securing tab. The elongated removal tabs extend beyond the frame and preferably have suitable structure, such as a first small diameter opening and an outwardly spaced second opening of larger diameter to allow fastening the removal tabs in a manner allowing for rapid and easy individual sequential removal of the tear-off lenses. The removal tabs are sufficiently flexible to enable folding thereof for securing the lens sheets to a post retaining member mounted on the goggle.

A transverse crease, which may be a line of perforation, can be included between the removal tab and the central lens portion to facilitate adherence of the tear-off lens to the goggle lens. The elongated removal tab may have first and second apertures for mounting the tab over a retaining post member which can be located on the goggle. The bottom tear-off lens of the stack includes adhesive for removably securing the tear-off lens stack to the main goggle lens.

The tearable lenses of the invention are of a desired shape, usually configured to generally correspond to the shape of the permanent goggle lens. The stack of tear-off lenses comprises a plurality of adhesively bonded transparent plastic sheets which have adhesive at the upper and lower peripheral portions thereof. The bonding strength of the adhesive is sufficient to provide adhesion of the tear-off lenses while enabling manual, serial separation and removal of the lenses from the stack.

Preferably, during fabrication of the tear-off lens stack, a layer of protective material, such as wax paper, for example, is applied over the adhesive of the bottom tear-off lens for protecting the adhesive until the time of intended use. If desired, the bottom lens in the tear-off lens stack could perform the function of the protective material, in which case the bottom adhesive layer could be omitted.

In accordance with another aspect of the invention, a goggle comprising a frame with a main goggle lens, together with a stack of tear-off lenses, as previously described, mounted thereover is provided. The goggle further includes a vertical opening or slot in the goggle at one side thereof into which a side peripheral portion or securing tab on each lens of the tear-off lens stack is insertable when in position over the main goggle lens for assisting in maintaining the tear-off lens stack in the mounted position. The goggle also includes a retaining post member at a side of the goggle opposite the side where the slot is located, for retaining the removal tabs in a desired position for facilitating removal.

In accordance with another aspect of the invention, a method of making a stack of tear-off goggle lenses of the type previously described is provided. The method includes: applying adhesive material over bottom portions of each of a plurality of flexible transparent lens webs corresponding to the upper and lower peripheral adhesively bonded together portions of the lens stack; bonding together the webs with the adhesive material while the webs are in registry to form a laminated web stack; and forming the webs, such as by cutting or stamping, for example, to form the tear-off lenses in the desired shape and size. In accordance with one embodiment of the method, the forming occurs after the bonding of the webs. In accordance with another embodiment, the method further includes applying a layer of protective material over the adhesive of the bottom web for protecting the adhesive material thereat. The adhesive material may be applied to the web as two linear strips and the webs can be bonded together to form a stack preform. Thereafter, the stack preform is formed to produce the stack of tear-off lenses of desired shape and size.

In accordance with a preferred embodiment of the invention, the adhesive that is utilized to bond the tear-off lenses together is a two-sided adhesive tape. Most preferably, one side of the tape has greater bonding strength than the other side. This allows the side of the tape with the greater bonding strength to be adhered directly to the bottom surface of each of the tear-off lenses so that between an outermost lens and the next lens in the stack, the adhesive tape remains adhered to the outermost lens when it is removed from the stack.

In accordance with still another aspect of the present invention, a kit for adapting a goggle for tear-off lenses is provided. The kit includes a retaining post member adapted for mounting on the frame of the goggle. The retaining post member can include a base portion, a cylindrical extension portion and an enlarged head portion. The kit also includes a stack of tear-off lenses as previously described, each tear-off lens including a securing tab at one end of the lens and an elongated removal tab at the opposite end of the lens, the securing tab being insertable into the goggle for securing the stack to the frame in conjunction with adhesively securing the stack to the main lens of the goggle, the elongated tab being securable to the post member when it is mounted on the goggle frame.

The stack of tear-off lenses provides for rapid mounting of a plurality of the lenses over the main lens of a goggle. This avoids the prior art disadvantage of the substantial time and effort required for individually positioning and mounting the tear-off lenses. Moreover, the tear-off lens stack of the present invention avoids scratching and soiling that can occur with known individual tearoff lenses.

BRIEF DESCRIPTION OF THE DRAWINGS

The present invention can be more completely understood by reference to the following detailed description in conjunction with the drawings, in which:

FIG. 4 is a top plan view of the goggle shown in FIG. 2;

FIG. 5 is an enlarged top plan view showing the initial attachment of the stack of tear-off lenses to the retaining post member of the goggle;

FIG. 6 is a cross-sectional view of FIG. 5 showing completion of attachment of the first tear-off lens of the lens stack to the goggle;

FIG. 7 is a side plan view of the retaining post member used for securing the tear-off lenses to the goggle frame;

FIG. 8 illustrates the manufacturing process used to produce a stack of tear-off lenses;

FIG. 9 illustrates the relative positions of the web used in the process shown in FIG. 8 to provide a stack of layered transparencies;

FIG. 10 illustrates a compressed preform stack of transparent lens sheets;

FIG. 11 illustrates the outline of the tear-off lenses to be formed from the preform stack of FIG. 10; and FIG. 12 illustrates a stack of tear-off lenses formed from the preform stack of FIG. 10.

DETAILED DESCRIPTION

Figure 1:
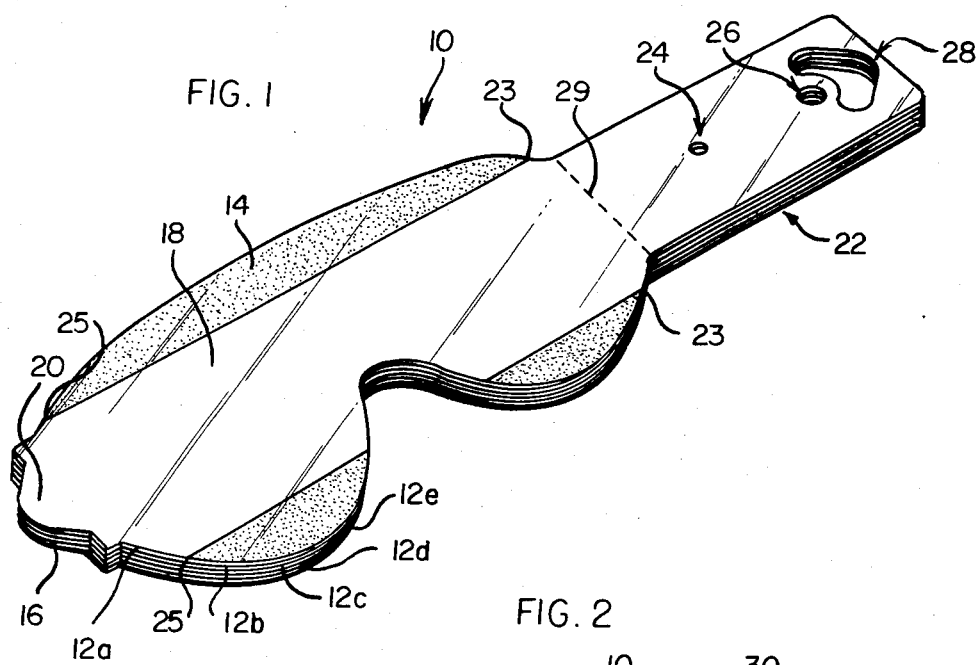
FIG. 1 is a perspective view of a stack of tear-off lenses according to the invention.

Referring to the drawings generally, where like reference numerals refer to like parts, and in particular to FIG. 1, there is illustrated a stack or book of tear-off lenses 10, which in this embodiment includes five tear-off lenses 12a–12e, and adhesive 14 located along upper and lower peripheral portions of the bottom of each lens 12. Greater or fewer tear-off lenses can make up a stack or book of lenses, as desired.

Stack 10 can also includes a layer of protective material 16, which in this case is wax paper, under bottom lens 12e and the adhesive thereon for protecting the adhesive on the bottom of lens 12e until stack 10 is ready for use, whereupon protective mater can be easily removed, such as by peeling it from bottom lens 12e.

Preferably, and as illustrated in FIG. 1, adhesive 14 on the bottom side of the upper and lower peripheral portions of each of lenses 12, comprises a two-sided tape on each of the upper and lower portions. Most preferably, the side of the tape that is adhered to the bottom surface of lenses 12 has a greater bonding strength than the other side of the tape. This allows the adhesive tape to remain on the topmost lens as it is being removed from the lens stack during use. Transparent polyester is a suitable material for the tape substrate or carrier, preferably having a thickness of about 0.5 mil. Adhesive 14 should permit manual separation of the lenses from the top to the bottom of stack 10. Suitable adhesives for use in accordance with the invention are known in the art and include adhesives such as acrylic resin-based adhesives, for example.

Lenses 12 of stack 10, each of which is manually serially removable therefrom from the top to bottom of stack 10, includes a central lens viewing portion 18 that usually generally corresponds to the shape of the main goggle lens. A securing and orientation tab portion 20 is provided at one end of stack 10 and an elongated removal tab 22 having a first opening 24 and a second opening 26 are located at the opposite end. The diameter of the first opening is less than that of the second opening to facilitate use of stack 10 as hereinafter described. An additional third opening 28 may also be provided to facilitate gripping removal tab 22 when it is desired to remove the outermost lens from stack 10.

The upper and lower peripheral portions of the adhesive 14 each taper towards a point 23 or other area of reduced size compared with the width of the adhesive near the middle locations along the lenses 12. This taper results in less adhesive where the lens 12 is first separated by action of the tab 22 and aids in peeling off the lens 12 without displacing the lower lenses before they are to be removed. A corresponding taper 25 at the opposite side of the adhesive also serves to minimize or prevent dislodging of the remaining lenses 12 as the topmost lens is removed.

As illustrated in FIG. 1, ech lens 12a–e includes a transverse crease 29 extending across lenses 12a–e, located between viewing portion 18 and removal tab 22. Crease 29 can be formed by any suitable method and can be a line of perforation, for example. In the illustrated embodiment, crease 29 facilitates the mounting and adherence of stack 10 to goggle 30 of FIGS. 2–6 as main goggle lens 36 is recessed within goggle frame 32 and the elongated removal tab 22 must curve upwardly and outwardly, as seen in FIG. 3, without forcing the lens 12a–e away from the surface of the main lens 36.

Figure 2:
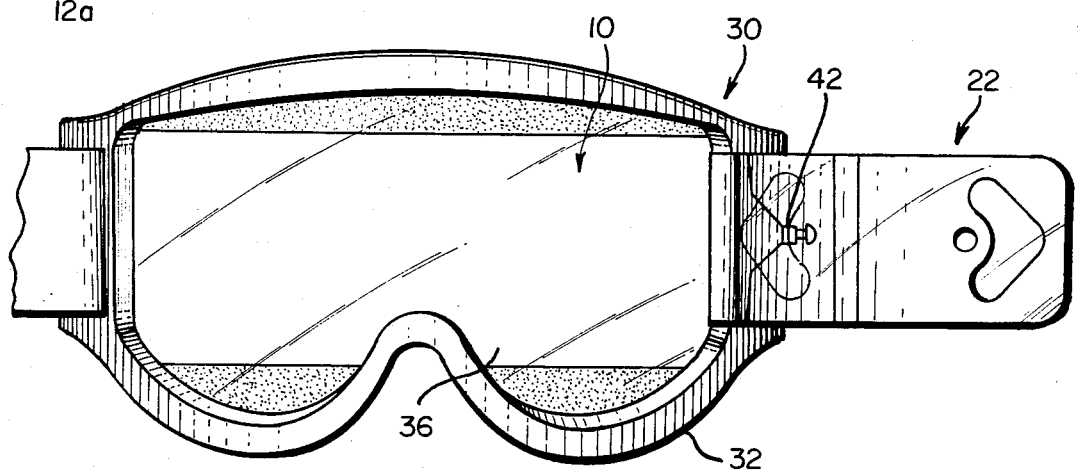
FIG. 2 is a front plan view of a goggle having a stack of tear-off lenses attached thereto.
Figure 3:
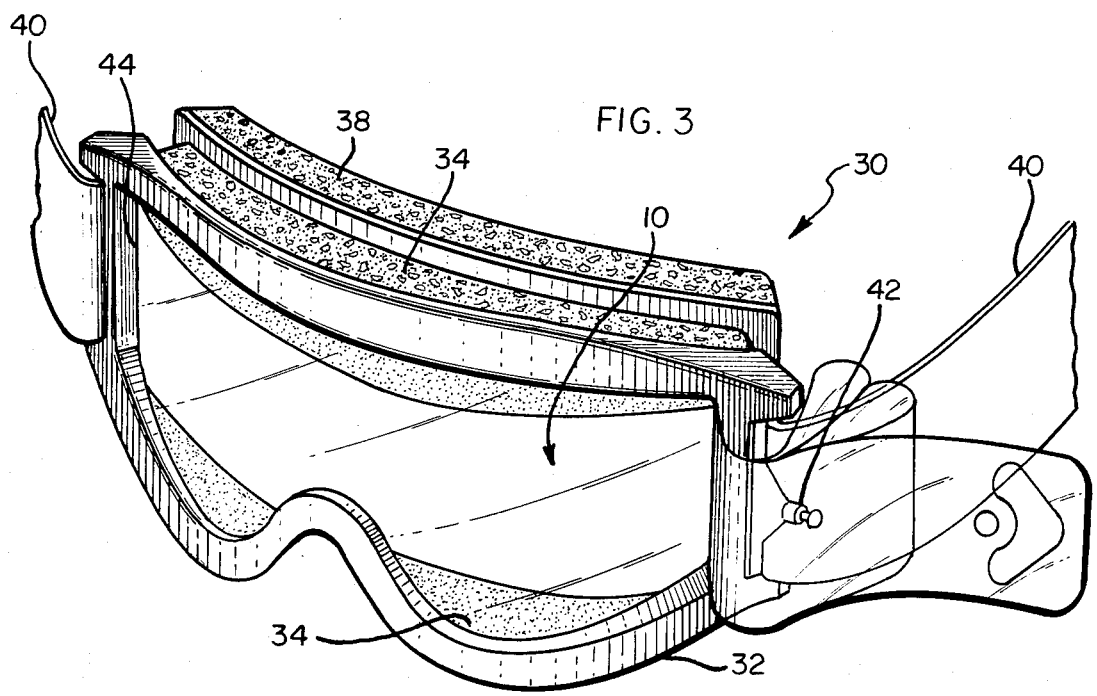
FIG. 3 is a perspective view of a goggle with the stack of tear-off lenses of FIG. 3.

A goggle 30 having stack 10 of tearable lenses 12 mounted thereon is shown in FIGS. 2–4. Goggle 30 includes a flexible frame 32, including foam-lined air vents 34, a main goggle lens 36, a foam liner or flange 38, an elastic headband 40 (partially illustrated) and a retaining post member 42, secured to frame 32. The general construction of frame 32, lens 36, foam-lined air vents 34 and foam liner 38 is disclosed in U.S. Pat. No. 3,945,044 to McGee, assigned to the assignee of the present application, the disclosure of which is hereby incorporated by reference. Frame 32 has an interior groove which mounts main goggle lens 36 therein. The sides of the lens 36 extend into the groove to form an opening or vertical slot 44 between the lens 36 and the frame 32. Since frame 32 and main goggle lens 36 are somewhat flexible, slot 44 can conform to the initial thickness of stack 10 and the reduced thickness as lenses 12 are removed therefrom.

Stack sheets 10 of tearable lenses 12 are easily attached to the goggle frame by removing protective material 16, inserting tab 20 into slot 44 located at the right-hand portion of the frame, which first serves to orient the stack so that the user correctly places the stack on the main lens, and then serves to help secure the stack, and subsequently attaching removal tabs 22 to retaining post member 42. Referring to FIG. 7, post member 42 is designed to be easily attached to goggle frame 32 by inserting post member end 45 into slot opening 46 provided in frame 32, which also allows headband 40 to be secured to frame 32. End 45 of post member 42, with a portion of the sidewall thereof, defines a z-shaped snap lock retaining portion 47 together with the interior of a complementary shaped portion of slot 46. While this type of post member is known per se, in another embodiment, the post hold down member can comprise a flat base with a glue-on adhesive surface which is secured to the main lens 36. This post would be a generic form usable with a wide variety of goggles of different manufacturers.

Referring to FIGS. 5–6, attachment of removal tabs 22a–e entails placing the smaller innermost first hole 24 over rounded head 48 of retaining post member 42. Hole 24 is slightly smaller in diameter than rounded head 48, but can be easily fitted thereover due to the flexibility of the plastic material employed for lens 12. Since hole 24 is smaller than head 48, tab 22 is secured behind head 48 on neck portion 50.

After securing tab 22e to retaining post 42, the remaining portion of tab 22e is folded back on itself so that, and as illustrated in FIG. 6, larger hole 26 is placed over head 48 onto neck portion 50.

As shown in FIG. 4, remaining securing tabs 22a–d of the stack are similarly mounted onto retaining post member 42. Topmost tab 22a of the stack only has innermost hole 24 mounted onto retaining post member 42. The remaining portion of tab 22a is left free to extend beyond the goggle frame so that the wearer can easily grasp it to remove the lens sheet. Upon removal of lens 12a, removal tab 22b of immediately underlying lens 12b automatically unfolds to extend beyond goggle frame 32. During riding, for example, a motorcyclist wearing the goggle can easily grasp the elongated member of the outermost transparency, pull it free of the post member and peel off the outer tear-off lens with one quick motion. When the outer elongated member is pulled free of the retaining post member, the elongated member of the immediately underlying transparency automatically unfolds, and is ready for grasping by the cyclist when it is time once again to remove another tear-off lens.

The stack of tearable lenses can be made by bonding together a plurality of adhesively coated plastic webs. As shown in FIGS. 8 and 9, webs 60a–e of transparent flexible plastic lens material are taken from rolls 62a-e and are contacted with adhesive tape 64a-e from adhesive tape rolls 66a-e. The tape rolls provide a two-sided adhesive tape 64a-e on the surface of webs 60a-e whereby the side of the tape with the greater bonding strength is adhered to the surface of each web that is the bottom surface in the finished tear-off lens stack. Web 60e and adhesive tape 64e has adhered thereto a protective material 68 which is a web of wax paper from roll 70. Coated webs 60a-e are passed through compression rollers 72, 72' to provide a laminated preform 74 as shown in FIG. 10. Preform 74 is cut to desired shape and size in cutter 78 to yield stacks 10. The crease line 29 can be created by a series of perforation holes formed by cutter 78. Conveyor 79 is utilized to transport the product as required.

FIG. 11 illustrates the outline of the cuts 80 to be made by cutter 78 to preform 74 (not showing wax paper sheet 68). FIG. 12 illustrates the resulting lens stack 10 with the bottom tear-off lens facing upwardly and the protective wax paper sheet removed.

It is to be understood that the process for making the tear-off lens stack in accordance with the invention can be accomplished in a variety of ways. For example, the shape of the individual lenses could be cut or formed, individually or as a web, prior to application of the adhesive and subsequent bonding together of the individual lens material layers. Also, adhesive material could be applied directly to the lens material without using adhesive tape, such as by spraying, rolling or brushing, for example.

A wide variety of transparent plastic materials may be employed for webs 60, as desired, and materials such as polyesters are particularly suitable. The thickness of the tear-off lens material may also vary as desired. Thicknesses of about 3 to 7 mils (1 mil=0.001/inch) are suitable with a preferred thickness being about 4 mils.

The width of adhesive tape 14 may be varied to suit the specific geometry of the permanent lens of the protective eye goggle and can also depend on the bonding strength of the adhesive. The total surface area covered by the tape should be sufficient to assure adequate adhesion of the members of the stack for the particular tear-off lens and goggle configuration utilized.

The stack of tearable lenses may be supplied to the user in the form of a kit. The kit includes a stack of tearable lenses 10 (as illustrated in FIG. 1, for example) and post retaining member 42, such as illustrated in FIG. 7, or the alternate embodiment previously described in which a generic form of post has a glue-on adhesive base secured to the main lens. Such a kit could be adaptable for use with a wide variety of goggles produced by different manufacturers.

While illustrative embodiments of the invention are shown in the drawings and are described in detail herein, the invention is susceptible of embodiment in many different forms. It should be understood that the present disclosure is to be considered as an exemplification of the principles of the invention and is not intended to limit the invention to the embodiments illustrated.

I claim:

1. A stack of tear-off lenses adapted for mounting to a goggle having a main goggle lens, said stack comprising: a plurality of flexible, transparent lenses adhesively bonded together by adhesive means only along upper and lower peripheral portions of each of said lenses, said lenses being manually serially removable from said stack, wherein each of said lenses has a viewing portion and an elongated removal tab at one end of said lens, wherein each of said lenses has a securing and orienting tab at the end of said lens opposite the end having the elongated removal tab, and said bottom tear-off lens including adhesive securing means for removal by securing said stack to said main goggle lens.

2. The stack of tear-off lenses of claim 1 wherein said adhesive means comprises a two-sided adhesive tape in which the side of the tape adhered to the bottom surface of each of the lenses has greater bonding strength than the other side of the tape so that the adhesive tape remains adhered to the outermost lens when the outermost lens is removed from said stack.

3. The stack of tear-off lenses of claim 1 wherein when mounted on a goggle said elongated portion extends beyond the frame of the goggle to facilitate manual serial removal of said lens from said stack.

4. The stack of tear-off lenses of claim 1 wherein said elongated removal tab includes first and second apertures for mounting over a retaining post member on the goggle.

5. The stack of tear-off lenses of claim 1 in which each tear-off lens further comprises a transverse crease therethrough between said removal tab and said viewing portion.

6. The stack of tear-off lenses of claim 1 further comprising a removable layer of protective material over said adhesive securing means on the bottom tear-off lens to protect said adhesive securing means until the time of intended use.

7. The stack of tear-off lenses of claim 1 wherein said adhesive securing means comprises a two-sided adhesive tape in which the side of the tape adhered to the bottom tear-off lens has greater bonding strength than the adhesive on the other side of said tape.

8. The stack of tear-off lenses of claim 1 wherein said adhesive securing means comprises an adhesive having a bonding strength sufficient to provide adherence of said stack to said main lens, yet which is removed from said main lens when said bottom tear-off lens is removed therefrom.

9. The stack of tear-off lenses of claim 1 wherein the adhesive means tapers to an area of reduced size adjacent the removal tab to minimize dislodging of remaining lenses when the topmost lens is manually removed.

10. The stack of tear-off lenses of claim 9 wherein the area of reduced size tapers to a first point on the upper peripheral portion and to a second point on the lower peripheral portion adjacent to the removal tab.

11. The stack of tear-off lenses of claim 9 wherein the adhesive means also tapers to an area of reduced size adjacent the securing tab.

12. A goggle comprising a goggle frame, a main lens mounted in said frame, a stack of tear-off lenses removably adhesively mounted in a position over said main lens, a vertical slot in said goggle at one side thereof into which a side peripheral portion of said stack is insertable when in position over said main lens for assisting in maintaining said stack in said mounted position, said goggle including a retaining post member at a side of said goggle opposite the side where said groove is located, said stack of tear-off lenses comprising a plurality of flexible transparent lenses adhesively bonded together with adhesive means provided only at the upper and lower peripheral portions of each of said lenses, each of said lenses being manually serially removable from said stack, wherein each of said tear-off lenses has a viewing portion, a securing tab defining said side peripheral portion at one end of said lens and an elongated removal tab at the opposite end of said lens, said elongated removal tab having an opening therethrough for mounting over said retaining post member located on said goggle frame.

13. The goggle of claim 12 wherein said stack is adhesively mounted and said tear-off lenses bonded together with two-sided adhesive tape on the bottom of each tear-off lens in which the side of the tape adhered to the bottom surface of each tear-off lens has greater bonding strength than the other side of the adhesive tape so that the adhesive tape remains adhered to the outermost lens when the outermost lens is removed from said stack.

14. The goggle of claim 13 wherein the bonding strength of said tape is sufficient to adhere said tear-off lenses together while enabling manual separation of the outermost sheet from said stack.

15. The goggle of claim 12 wherein said vertical slot is formed by cooperation of said goggle frame and said main goggle lens.

16. The goggle of claim 15 in which said goggle frame and said main goggle lens are flexible so that said vertical slot can conform to the thickness of the tear-off lenses in said stack.

17. The goggle of claim 12 wherein the adhesive means reduces in cross sectional area adjacent at least one of the tabs to minimize dislodging of remaining lenses in the stack when removing the topmost lens.

18. A method of making a stack of tear-off goggle lenses comprising a plurality of flexible transparent lenses adhesively bonded together only along upper and lower peripheral portions of said lenses, each of said lenses being manually serially removable from said stack and of a desired shape and size and the bottom tear-off lens in said stack including adhesive for removably securing said stack to a goggle lens, said method comprising applying adhesive material over bottom portions of each of a plurality of flexible transparent lens webs corresponding to the upper and lower peripheral adhesively bonded together portions of said lenses, bonding together said webs with said adhesive material while said webs are in registry to form a laminated web stack and cutting said webs to form said tear-off lenses in the desired shape and size.

19. The method of claim 18 wherein said cutting occurs after said bonding together of said webs.

20. The method of claim 18 further comprising applying a layer of protective material over the adhesive of said bottom web to protect the adhesive material on said bottom web.

21. The method of claim 20 wherein said layer of protective material is applied prior to said bonding together of said webs.

22. The method of claim 18 wherein said adhesive material is a two-sided adhesive tape in which the side of the tape with the greater bonding strength is adhered to the bottom surface of said web.

23. The method of claim 18 wherein the adhesive material is applied to said webs as a linear strip and thereafter said webs are bonded together to form a stack preform and thereafter said stack preform is cut to form said stack of tear-off lenses.

24. A kit for adapting a goggle having a main lens for tear-off lenses, comprising a post member adapted for mounting on the frame of the goggle, a stack of tear-off lenses having a plurality of flexible transparent lenses adhesively bonded together by adhesive means only along upper and lower peripheral portions of each of said lenses, each of said lenses being manually serially removable from said stack wherein each of said lenses has a viewing portion, a securing tab at one end of said lens and an elongated removal tab at the opposite end of said lens, said securing tab being insertable into the goggle for facilitating securing of said stack to said frame, said elongated tab being securable to the post member when mounted relative to the goggle frame, and said bottom tear-off lens including adhesive securing means for removably securing said stack to the main goggle lens.

25. The kit of claim 24 wherein said adhesive means comprises a two-sided adhesive tape in which the side of the tape adhered to the bottom surface of each tear-off lens has greater bonding strength than the other side of the adhesive tape so that the adhesive tape remains adhered to the outermost lens when the outermost lens is removed from the stack.

* * * * *